United States Patent [19]

Luft

[11] 3,968,369

[45] July 6, 1976

[54] NON-DISPERSIVE INFRARED GAS ANALYSIS DEVICE WITH TRIPLE LAYER RECEIVER

[75] Inventor: Karl Friedrich Luft, Essen, Germany

[73] Assignee: Bergwerksverband GmbH, Essen, Germany

[22] Filed: Nov. 15, 1974

[21] Appl. No.: 524,249

[52] U.S. Cl. ................................. 250/344; 250/345
[51] Int. Cl.² ........................................ G01N 21/26
[58] Field of Search ..................... 250/343, 344, 345

[56] References Cited
UNITED STATES PATENTS 3,215,832   11/1965   Madsen et al. .................. 250/344
3,529,152   9/1970   Strange et al. .................. 250/344 X
3,770,974   11/1973   Fertig ................................. 250/344

Primary Examiner—Davis L. Willis
Attorney, Agent, or Firm—Malcolm W. Fraser

[57] ABSTRACT

A radiation receiver including three receiver layers for infrared gas analysis. The first and third layers are connected in parallel, and their pressure is compared with that of the second or middle layer to derive a pressure difference which compensates for certain measurement problems found in prior art devices.

5 Claims, 5 Drawing Figures

NON-DISPERSIVE INFRARED GAS ANALYSIS DEVICE WITH TRIPLE LAYER RECEIVER

BACKGROUND OF THE INVENTION

1. Field of the Invention

The invention relates to a non-dispersive infrared gas analysis device wherein, according to German Pat. 1,017,385 and corresponding U.S. Pat. 2,951,939, radiation detection is carried out in two receiver layers arranged in series in the path of rays.

2. Description of the Prior Art

The invention aims at an improvement of this measuring principle in several respects, particularly by reduction of interference effects caused by the unsymmetrical structure of such two-layer receivers and noticeable at difficult conditions of measurement, as they prevail, for instance, in the field of environmental protection and safety control in mining. They prevail, for example, when very small traces of a toxic gas, such as carbon monoxide, are to be measured in the presence of high concentrations of other gases which are likewise infrared radiation-absorbing and when, moreover, high stability and accuracy in the measurement is required.

SUMMARY OF THE INVENTION

In the invention, instead of two receiver layers arranged in series in the path of rays, three layers are employed. The first layer impinged upon by radiation is pneumatically connected with the third layer. The temperature or pressure difference occurring because of radiation absorption between these two layers and the middle receiver layer is measured by means of a suitable measuring element, for example, a diaphragm capacitor.

Because of the strong preabsorption in the first two receiver layers, the third receiver layer, which is the last layer impinged upon by the radiation, changes the absorption conditions for the receiver gas itself only to a relatively small degree, but this third layer is extremely effective for the compensation of interference effects. Thus, the third receiver layer may, for example, serve to compensate the interference signals produced by the overlapping of the absorption bands of the receiver gas with those of other gases. In contrast to the absorption within the bands of the receiver gas which are already strongly saturated in the first two layers, the radiation, which is scarcely weakened by the small pre-absorption in the overlapping area, has a full effect in the third layer.

At weak absorption, as it occurs in many interference gases in the overlapping area of the bands, an approximately equal radiation energy is therefore absorbed in each layer thickness unit of the receiver layers. When therefore the sum of the thicknesses of the first and third layer equals the thickness of the middle layer, the interference effect produced by the band overlapping is compensated. The arrangement offers a special additional advantage when the the layer thicknesses of the first and third layer are equal. It is known (see, e.g., M. Golay, Rev. Sci. Instrum., vol. 18, No. 5, page 354 (1947)) that the sensitivity to vibrations caused by the inertia forces which act upon the gas filling of the receiver chambers of thermopneumatic radiation detectors disappears when the centers of gravity of the gas masses acting at both sides of the measuring element, such as the diaphragm capacitor, coincide. This condition, however, is fulfilled precisely when the receiver chamber system is symmetrically constructed and provided with two equal, pneumatically cooperating chambers and a central, pneumatically counteracting chamber.

The triple-layer receiver can be constructed in various ways and inserted in known photometer arrangements.

Thus, the rear wall of the third receiver chamber can be made reflective, so that the radiation not yet absorbed passes once more through the chamber (FIG. 1a).

The rear wall of the third receiver chamber may, however, also be constructed as a radiotransparent wall, and may irradiate measuring or reference radiation into the chamber system from opposite directions (FIG. 2a).

The invention contains, moreover, further possibilities of adaptation to difficult measuring problems. If the middle chamber is constructed so as to be displaceable with respect to the first and third (FIG. 3), a suitable adjustment also permits compensation of interference signals for interference gases wherein the absorption in the overlapping areas is stronger and therefore no longer increases in proportion to the layer thickness.

Since the receiver chambers of the triple-layer receiver are cylindrical and the middle chamber is generally longer than the two outer ones, difficulties arise in the compensation produced in the difference formation of the radiation modulated by absorption, as a result of the fact that the thermopneumatic time constant of the middle chamber, due to the larger volume and the smaller heat discharge thereof, is greater than that of the two outer chambers.

These compensation difficulties produced by the phase differences of the chamber signals can be largely removed, in a manner similar to that prevailing in the known two-layer receivers, by shaping the middle chamber in a specific way.

When the cylindrical shape is retained, the thermopneumatic time constant of the middle chamber is adapted to that of the outer chambers by producing an additional heat discharge, for example, by means of a body mounted along the chamber axis, for instance a metal rod.

BRIEF DESCRIPTION OF THE DRAWINGS

With the aid of FIGS. 1–3, the invention and the various embodiments thereof will be explained in greater detail in the following.

DESCRIPTION OF THE PREFERRED EMBODIMENTS

Figure 1A:
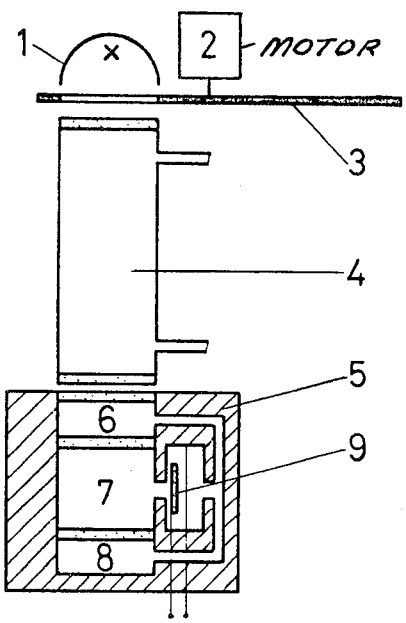
FIG. 1a illustrates a triple-layer receiver.

FIG. 1a shows the triple-layer receiver with reflecting rear wall of the third receiver chamber in the simple beam photometer arrangement. The infrared radiation issuing from an emitter 1 is periodically interrupted by means of a rotating shutter 3 driven by a motor 2. After passing through the vessel 4 which contains the gas mixture to be tested, the modulated radiation successively enters the receiver chambers 6, 7, and 8 of a triple-layer receiver 5. The mode of operation of the two chambers 6 and 7 is the same as in the known two-layer receiver according to German Pat. No. 1,017,385, that is, radiation is absorbed in the front chamber 6 chiefly in the centers, and in the second chamber 7, which is generally longer, the radiation is absorbed in the sides of the lines of rotation and bands of the receiver gas. The pressure difference thus produced is measured by means of the measuring element, such as, a diaphragm capacitor 9. For the third chamber 8, essentially only radiation in the spectral region is left, in which absorption is still smaller, which are therefore even more distant from the points of maximum absorption. The third chamber becomes thus fully effective only in the wavelength areas of the radiation wherein usually an overlapping of the absorption bands of the receiver gas with the bands of interference gases takes place. This is the cause of the so-called cross sensitivity to other, likewise infrared-radiation-absorbing gases. By means of the third chamber, which is connected pneumatically in parallel with the first chamber, it is therefore possible to compensate efficiently the generally negative cross sensitivity resulting from the greater length of the second chamber. That is, it is possible to suppress efficiently the differential signal occurring at signal detector 9, due to the effect of such cross sensitivity, which signal detector is shown in FIG. 1a as diaphragm capacitor.

If, in addition, chambers 6 and 8 are of the same lengths and diameters, the common center of gravity of these chambers coincides with that of the middle chamber, and as a result, the already mentioned insensitivity of the thermopneumatic detector to accelerated movements due, for example, to vibrations occurs.

Figure 1B:
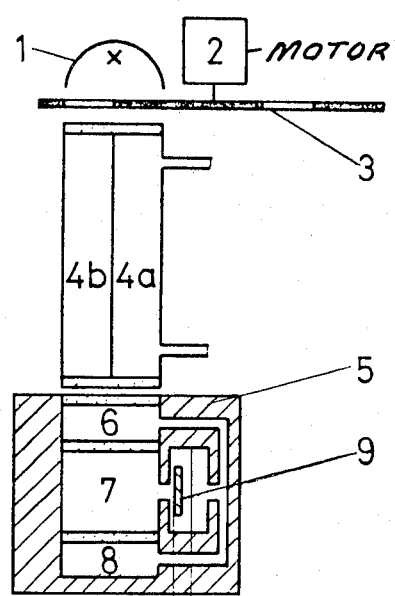
FIG. 1b illustrates a triple-layer receiver with a divided chamber for providing both measuring and reference rays.

In the arrangement of FIG. 1b, the radiation is divided by the divided chamber 4a and 4b into a measuring and a reference path of rays, and the two paths of rays are modulated, in an in-phase opposed manner, by means of the correspondingly shaped rotating shutter 3. As in the two-layer receiver in the arrangement of German Pat. No. 1,302,592 and U.S. Pat. No. 3,162,761, the interference signals which occur in the triple-layer receiver by imperfect compensation of the chamber signals are thus largely eliminated.

Figure 2A:
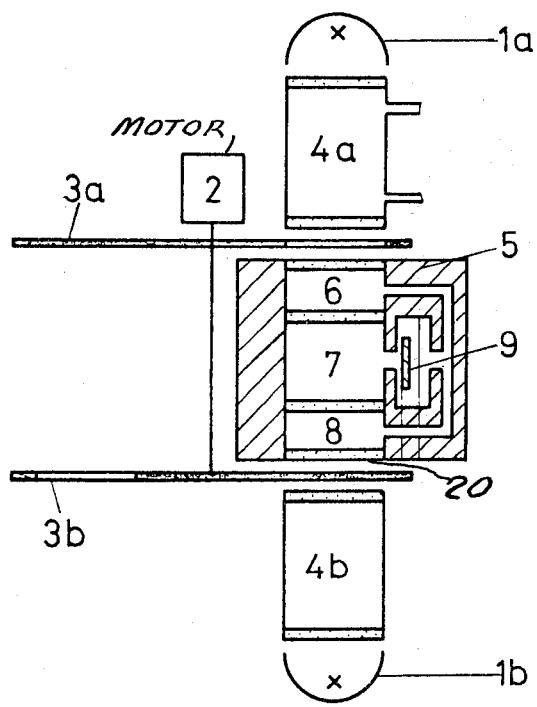
FIG. 2a illustrates a triple-layer receiver using a radio transparent rear wall.

FIG. 2a shows the embodiment of the triple-layer receiver with radiotransparent rear wall 20 of receiver chamber 8. The reference radiation which is produced with the aid of a second emitter 1b and, after passing through a reference vessel 4b, enters receiver chamber 8 is modulated, as in the arrangement of FIG. 1b, in an in-phase opposite manner with respect to the measuring path of rays by means of a shutter 3b.

Figure 2B:
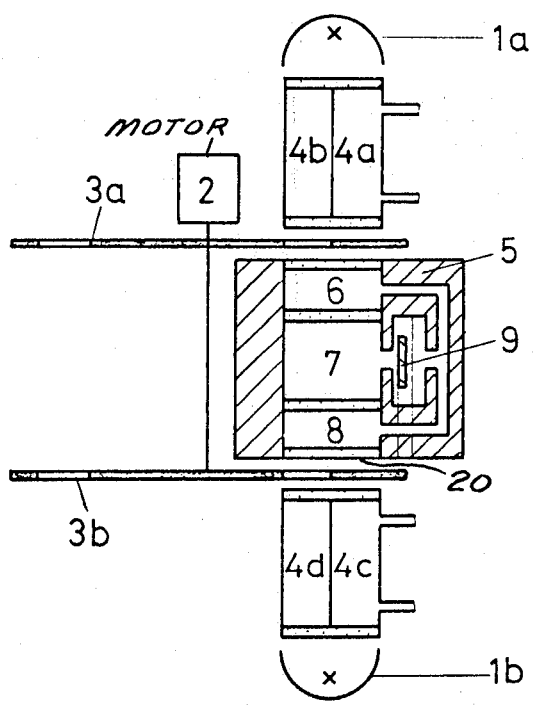
FIG. 2b illustrates a system according to FIG. 2a wherein two divided chambers are provided.

A further modification is shown in the arrangement of FIG. 2b wherein each of the two chambers 6 and 8 is impinged upon by two radiations which, with the aid of emitters 1a or 1b, the half vessels 4a and 4b, or 4c and 4d, and rotating shutters 3a or 3b, are modulated in an in-phase opposite manner. In this structure, the mutual adjustment of rotary shutters 3a and 3b is selected in such a way that the interference signals are compensated and the measuring signals are added together.

Figure 3:
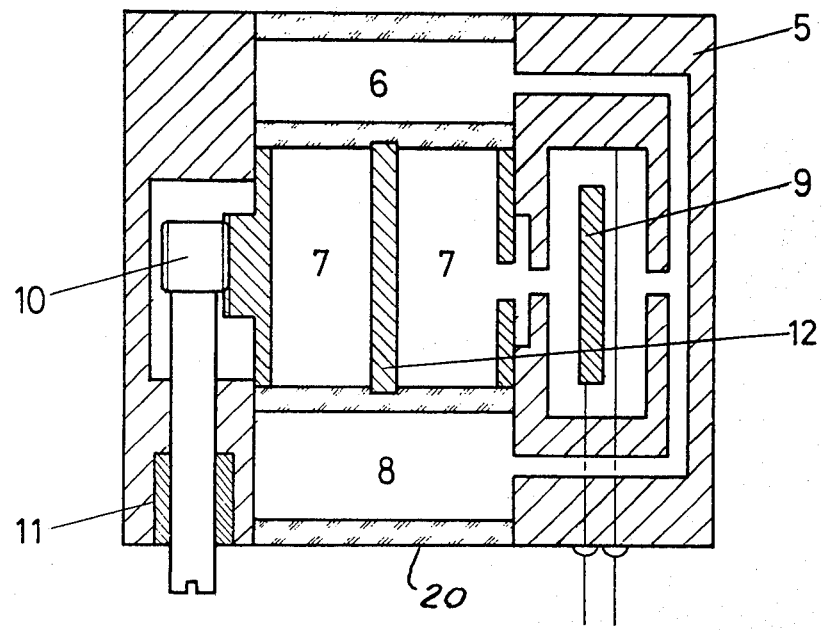
FIG. 3 illustrates a three-layer receiver wherein the middle layer or chamber can be displayed from outside the device.

FIG. 3 shows the embodiment of the triple-layer receiver wherein the middle chamber 7 can be displaced from the outside with respect to the outer chambers 6 and 8 by means of a screw 10 which passes through a vacuum-tight passage 11. Besides, a metal rod 12 is mounted in the axis of the middle chamber 7, with the aid of which rod by means of a suitable dimensioning of its diameter, the thermalpneumatic time constant of this chamber is adapted to that of the outer chambers.

What is claimed is:

1. Non-dispersive infrared gas analysis device for use with a set of incoming infra-red rays, comprising:
   A. a radiation receiver divided into first, second, and third receiver layers arranged in series in the path of said rays, the first and third layers being outer layers and the second layer being a middle layer, and
   B. pneumatic parallel connection means for the first and the third layers, whereby a pressure difference occurs, due to radiation absorption, between the connected first and third layers at one pressure and the middle layer at another pressure, and
   C. means for measuring the pressure difference.

2. A device according to claim 1 wherein the means for measuring is a diaphragm capacitor.

3. A device according to claim 1, wherein the third receiver layer has a rear wall formed by a radio-transparent window through which a second set of infra-red rays is likewise fed to the receiver.

4. A device according to claim 1 wherein each layer comprises a chamber.

5. Non-dispersive infrared gas analysis device for use with incoming rays comprising:
   A. at least one radiation source for infrared rays,
   B. at least one rotating shutter for modulation of the infrared rays,
   C. at least one vessel for a gas mixture to be tested, the vessel being situated in the path of the modulated incoming infrared rays,
   D. a radiation receiver divided into first, second, and third receiver layers arranged in series in the path of said rays through the vessel, the layers being separated by radio-transparent windows for the admittance and exit of the rays, the first and third layers being outer layers and the second layer being a middle layer, the third layer having a rear wall opposite the admittance window,
   E. pneumatic parallel connection means for the first and third layers, whereby a pressure difference occurs, due to radiation absorption, between the connected first and third layers at one pressure and the middle layer at another pressure, and
   F. means for measuring the pressure difference.

* * * * *